(12) United States Patent
Kim et al.

(10) Patent No.: US 7,758,626 B2
(45) Date of Patent: Jul. 20, 2010

(54) DEVICE AND METHOD FOR DELIVERING AN ENDOVASCULAR STENT-GRAFT HAVING A LONGITUDINALLY UNSUPPORTED PORTION

(75) Inventors: Andrew J. Kim, Santa Rosa, CA (US); Eric D. Johnson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1016 days.

(21) Appl. No.: 10/894,667

(22) Filed: Jul. 20, 2004

(65) Prior Publication Data

US 2006/0020319 A1    Jan. 26, 2006

(51) Int. Cl.
*A61F 2/06* (2006.01)
*A61F 11/00* (2006.01)

(52) U.S. Cl. .............. 623/1.11; 623/1.13; 623/1.23; 606/108

(58) Field of Classification Search ............. 623/1.11, 623/1.12, 1.15, 1.16, 1.17, 1.13, 1.23, 1.25
See application file for complete search history.

(56) References Cited

U.S. PATENT DOCUMENTS

| | | | | | |
|---|---|---|---|---|---|
| 4,562,596 | A | * | 1/1986 | Kornberg | 623/1.32 |
| 4,585,000 | A | * | 4/1986 | Hershenson | 606/194 |
| 5,279,565 | A | * | 1/1994 | Klein et al. | 604/105 |
| 5,387,235 | A | * | 2/1995 | Chuter | 623/1.11 |
| 5,683,451 | A | | 11/1997 | Lenker et al. | 623/1.11 |
| 5,713,907 | A | * | 2/1998 | Hogendijk et al. | 606/108 |
| 5,713,917 | A | | 2/1998 | Leonhardt et al. | 606/194 |
| 5,720,776 | A | * | 2/1998 | Chuter et al. | 623/1.36 |
| 5,817,102 | A | * | 10/1998 | Johnson et al. | 606/108 |
| 5,824,055 | A | * | 10/1998 | Spiridigliozzi et al. | 623/1.11 |
| 5,871,536 | A | | 2/1999 | Lazarus | 623/1.13 |
| 5,957,949 | A | | 9/1999 | Leonhardt et al. | 623/1.24 |
| 5,968,053 | A | * | 10/1999 | Revelas | 606/108 |
| 6,024,763 | A | | 2/2000 | Lenker et al. | 606/191 |
| 6,053,943 | A | * | 4/2000 | Edwin et al. | 623/1.25 |
| 6,110,198 | A | | 8/2000 | Fogarty et al. | 623/1.12 |
| 6,168,616 | B1 | | 1/2001 | Brown, III | |
| 6,312,462 | B1 | * | 11/2001 | McDermott et al. | 623/1.25 |
| 6,582,460 | B1 | * | 6/2003 | Cryer | 623/1.11 |
| 6,994,722 | B2 | * | 2/2006 | DiCarlo | 623/1.13 |
| 7,485,139 | B1 | * | 2/2009 | Ciamacco, Jr. | 623/1.11 |
| 2001/0023369 | A1 | * | 9/2001 | Chobotov | 623/1.11 |
| 2002/0019665 | A1 | * | 2/2002 | Dehdashtian et al. | 623/1.35 |
| 2002/0188344 | A1 | * | 12/2002 | Bolea et al. | 623/1.11 |
| 2003/0135257 | A1 | * | 7/2003 | Taheri | 623/1.11 |

(Continued)

FOREIGN PATENT DOCUMENTS

WO    WO 94/27667    12/1994

(Continued)

*Primary Examiner*—(Jackie) Tan-Uyen T Ho
*Assistant Examiner*—Jing Ou
(74) *Attorney, Agent, or Firm*—Al Ferro (57) ABSTRACT

An endoluminal prosthesis having an unsupported or flexible region and a delivery system for delivering the endoluminal prosthesis is provided. The delivery system includes a prosthesis delivery catheter with stiffening elements that provide longitudinally rigid support to a flexible or unsupported portion of an endoluminal prosthesis as the prosthesis is being deployed. A prosthesis is removably coupled to the stiffening elements. The endoluminal prosthesis can be a stent or a stent graft or graft.

1 Claim, 6 Drawing Sheets

U.S. PATENT DOCUMENTS

2003/0176912 A1* 9/2003 Chuter et al. .............. 623/1.13
2003/0216802 A1* 11/2003 Chobotov ................. 623/1.13
2004/0093057 A1* 5/2004 Bolduc et al. ............. 623/1.11
2005/0182290 A1* 8/2005 Lau et al. ...................... 600/37

FOREIGN PATENT DOCUMENTS

| WO | WO 97/07751 | 3/1997 |
| WO | WO 98/42276 | 10/1998 |
| WO | WO 01/97715 | 12/2001 |
| WO | WO 02/41805 | 5/2002 |

* cited by examiner

DEVICE AND METHOD FOR DELIVERING AN ENDOVASCULAR STENT-GRAFT HAVING A LONGITUDINALLY UNSUPPORTED PORTION

FIELD OF THE INVENTION

The present invention relates to tubular prostheses such as grafts and endoluminal prostheses for placement within or in place of a body lumen including, for example, stent-grafts, aneurysm exclusion devices, stents or grafts, (including, e.g., semi-supported, unsupported, coronary and peripheral prostheses) and to devices and methods for placement of such endoluminal structures.

BACKGROUND OF THE INVENTION

A wide range of medical treatments have been previously developed using "endoluminal prostheses," which term is herein intended to mean a medical device adapted for temporary or permanent implantation within a body lumen, including both naturally occurring or artificially made lumens. Examples of lumens in which endoluminal prostheses may be implanted include, without limitation: arteries such as those located within coronary, mesentery, peripheral (including, e.g., abdominal and thoracic aorta), or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

A number of vascular devices have been developed for replacing, supplementing or excluding portions of blood vessels. These vascular grafts may include but are not limited to endoluminal vascular prostheses and stent grafts, for example, aneurysm exclusion devices such as thoracic aortic aneurysm ("TAA") devices that are used to exclude aneurysms and provide a prosthetic lumen for the flow of blood.

A very significant use for such endoluminal or vascular prostheses is in treating aneurysms. Vascular aneurysms are the result of abnormal dilation of a blood vessel, usually resulting from disease or a genetic predisposition, which can weaken the arterial wall and allow it to expand. While aneurysms can occur in any blood vessel, most occur in the aorta and peripheral arteries, and particularly the abdominal and thoracic aorta.

Aneurysms have been treated by implanting tubular prostheses within a body lumen to provide a lumen or lumens for blood flow while excluding blood flow to the aneurysm site. They are introduced into a body lumen using a catheter to place the endoluminal prosthesis at the diseased site within the body lumen. Many of the aneurysm exclusion devices are self-expanding and expand inside the body lumen as they are being released from the catheter. They typically securely engage a vessel wall above and below the aneurysm site to exclude the aneurysm site from the flow of blood.

Typically these endoluminal prostheses or stent grafts are constructed of graft materials such as woven polymer materials (e.g., Dacron, or expanded-polytetrafluoroethylene ("ePTFE")) secured to the inner or outer diameter of a support structure including a plurality of annular members. The annular members provide sufficient radial force so that the prosthesis engages the inner lumen wall of the body lumen to hold the graft material in place against a lumen wall to exclude the flow of blood through the prosthetic lumen from the aneurysm.

The support structure in most endoluminal prostheses include some type of longitudinal support mechanisms, e.g., between annular supports structures. Longitudinal supports such as, e.g., a bar extending the length or a portion of the length of the graft have been used in a variety of different stent-grafts. Other types of longitudinal support may include, e.g., individual connecting elements between adjacent stent rings, or a fully supported stent structure (e.g., the AneuRx® stent graft). The longitudinal support mechanism provides columnar support when the device is loaded in a catheter, preventing kinking and wrinkling of the graft material when the device is deployed; and the support member further provides columnar support for the device when in place in vivo. However, such support mechanisms reduce the device flexibility when deployed, making it difficult to place the device in a particularly curved or tortuous vessel lumen. Furthermore, a stiff body such as that of a longitudinally supported prosthesis may be more prone to kink in a manner that leads to vessel occlusion. The columnar support elements hinder deliverability to some degree by presenting a stiffer catheter body. Also, the columnar support elements in many situations must be lined up in certain orientations making delivery more complex. Finally, the stresses on columnar support elements can cause them to fracture.

Accordingly, it would be desirable to provide a delivery system that eliminates the need for a longitudinal support member in deployment. It would also be desirable to eliminate device fatigue associated with longitudinal support members and subsequent breaks and fractures. It would also be desirable to provide a flexible endoluminal prosthesis for a more simplified deployment in curved or tortuous vessels. It would also be desirable to provide a delivery system and method for delivering a graft device that avoids wrinkling and kinking.

Mechanisms have been used in delivery systems to facilitate stent-graft delivery and reduce deployment force. For example, runners within the catheter along the outside of the prosthesis length have been used to reduce friction during deployment between the sheath and the prosthesis. The runners have been particularly useful where the support structures are located on the outside of the graft material and tend to engage the inner circumference of the sheath covering the prosthesis. However, the runners tend to be difficult to retract back into the catheter because after deployment they end up between the vessel wall and the expanded prosthesis. Furthermore, these mechanisms do not provide a means for reducing deployment force of a prosthesis having an unsupported portion.

It would also be desirable to provide a mechanism for reducing the force required to deploy a flexible or minimally supported prosthesis.

SUMMARY OF THE INVENTION

Embodiments according to the present invention provide a delivery system for a flexible endoluminal prosthesis or an endoluminal prosthesis with a flexible portion. In one embodiment, the endoluminal prosthesis is a stent graft with a portion of the graft unsupported by a support structure. A delivery system is configured to reduce deployment force required when deploying an endovascular prosthesis with minimal longitudinal support or with one or more flexible portions. A delivery system can be configured to avoid graft kinking or wrinkling during deployment of a graft prosthesis.

In particular, a delivery system in accordance with the invention includes stiffening elements removably coupled to the endoluminal prosthesis for deployment, and that provide support to a flexible or unsupported portion of an endoluminal prosthesis as the prosthesis is being deployed. The prosthesis includes a coupling device for removably coupling the stiffening elements to the prosthesis during deployment. According to one variation, the prosthesis comprises receiving elements for removably receiving the stiffening elements.

An endoluminal prosthesis according to one variation comprises a tubular member constructed of a graft material and at least one annular support member. The tubular member includes, a proximal opening and a distal opening providing a lumen through which body fluids may flow. When deployed, the tubular graft is maintained in a conformed (sealing arrangement) with the inner wall of a body lumen. The tubular graft is formed of a material such as a woven fiber or other suitable material for conducting fluid. In accordance with one embodiment, the prosthesis is sufficiently flexible that, when deployed in a curved position, it permits bending of the prosthesis to conform to the curvature of the vessel and reduces stresses on the prosthesis structures.

According to one variation, the prosthesis includes pockets for receiving stiffening members, formed or sewn onto the graft material of graft prosthesis.

Stiffening elements according to the invention may be stiffening bars coupled to the catheter and extending along the distal portion of the catheter when the prosthesis is loaded.

In general, the endoluminal prosthesis is radially compressed and loaded on or may otherwise be coupled to, the distal end of the catheter for delivery to the deployment site. Stiffening bars extend at least along the unsupported portion of the prosthesis and are removably attached to the prosthesis. The prosthesis is deployed out of the catheter in one of several manners generally known in the art. The stiffening elements are coupled to the prosthesis in a manner that permits the stiffening elements to push the prosthesis from the catheter and/or to support the prosthesis during deployment from the catheter. The stiffening elements may then be removed from the prosthesis and retracted back into the catheter.

In one variation, stiffening elements are inserted into the receiving elements or pockets. The prosthesis is constrained, e.g., by a sheath covering the prosthesis and/or by a restraining element such as a breakable suture, while the catheter is tracked to the deployment site using an imaging technique such as fluoroscopy. Once appropriately located, the restraining element is released or the sheath covering the tubular graft is retracted while the stiffening elements support the prosthesis opposing the compressive deployment forces. As the prosthesis is released, the annular members expand and attach or engage the prosthesis to the inner wall of the body lumen. Once the prosthesis is in place, the inner member of the catheter and the stiffening elements are retracted back into the catheter, the stiffening elements thus being withdrawn from the coupling device, e.g., receiving elements, of the prosthesis. The flexible or unsupported portion of the prosthesis is then permitted to bend or flex according to the anatomy and as blood is pumped through the lumen of the prosthesis.

The endoluminal prosthesis may be, for example, a stent, a graft or a stent graft. The coupling mechanism may be coupled to the support mechanism of the prosthesis or if applicable, to the graft material.

These and further aspects of the invention are exemplified and in the detailed description of embodiments according to the invention described below.

DETAILED DESCRIPTION

Figure 1A:
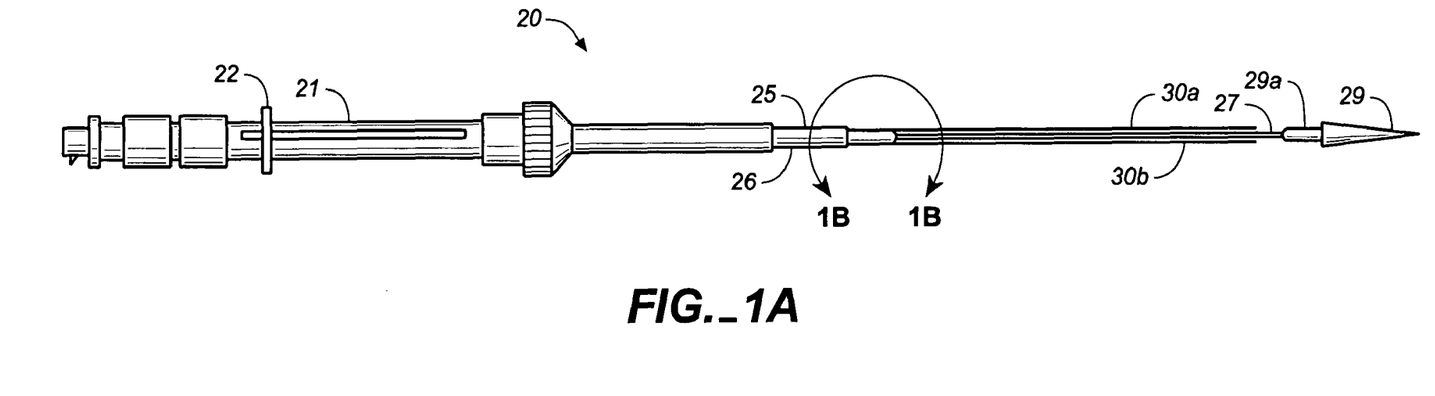
FIG. 1A is a side view of a delivery catheter according to the invention.
Figure 2:
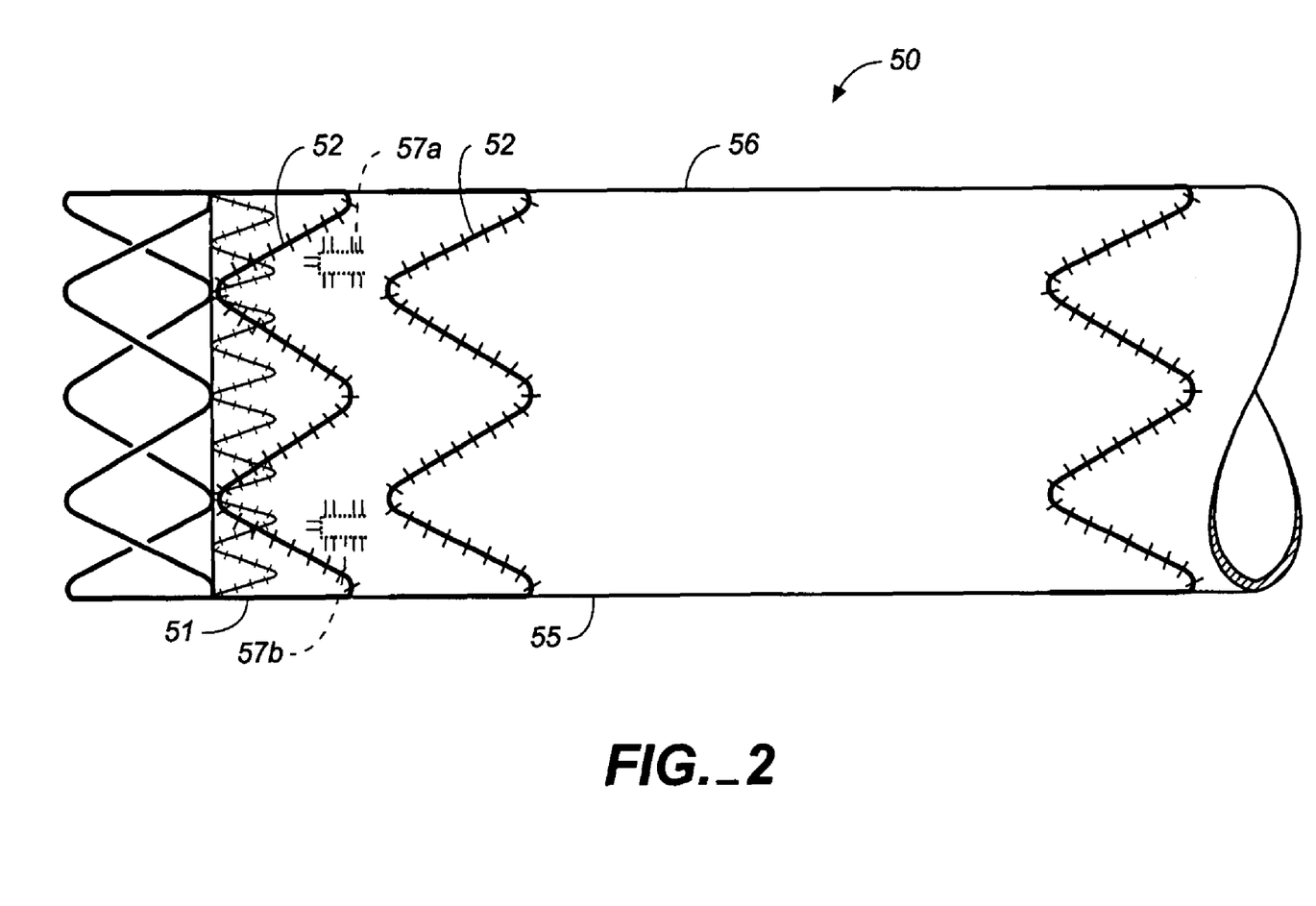
FIG. 2 is a partial side view of an expanded endoluminal prosthesis according to the invention.
Figure 3A:
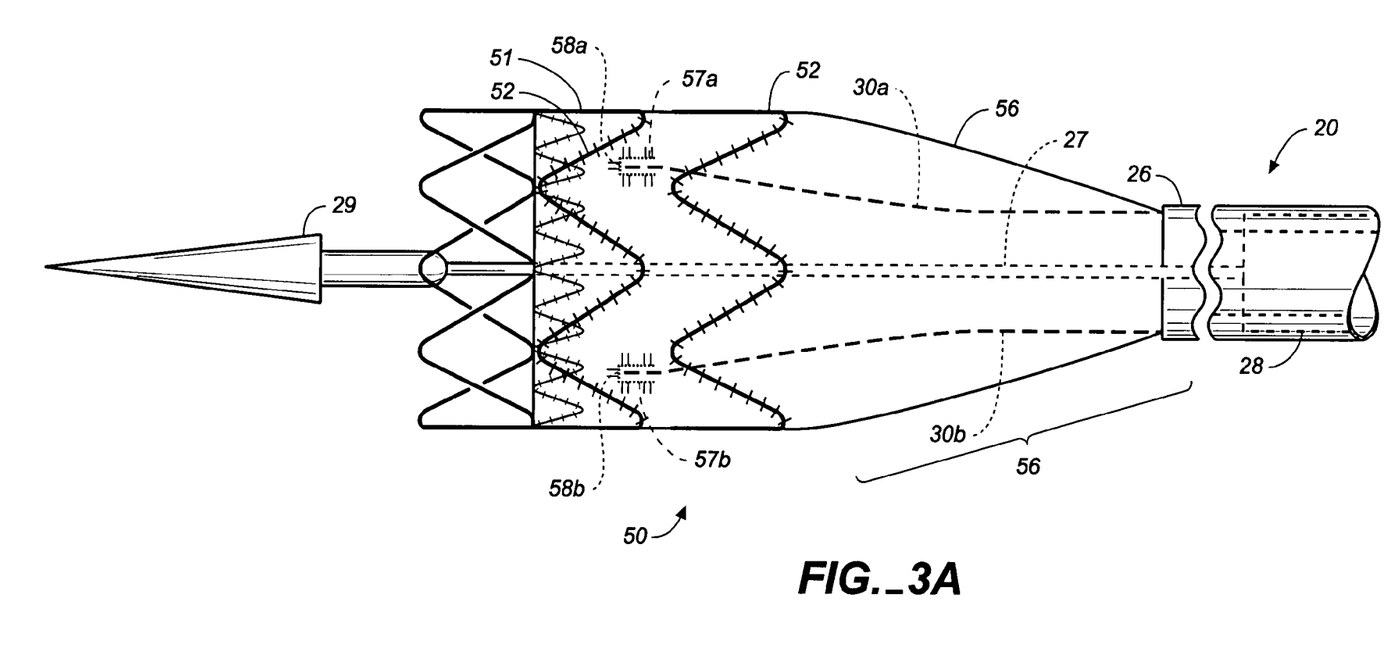
FIG. 3A is a side view of the endoluminal prosthesis of FIG. 2 according to the invention as it is being delivered by the catheter of FIG. 1A.

Referring to FIG. 1A a catheter 20 is illustrated comprising a proximal handle portion 21 and a distal delivery portion 25. An inner member 27 extends from the proximal portion 21 through the distal portion 25 of the catheter 20 and has a guidewire lumen therethrough for receiving a guidewire to guide the catheter 20 to a site for deployment of an endoluminal prosthesis 50 (FIGS. 2 and 3). The proximal handle portion 21 includes a slidable ring 22 for retracting a sheath 26 that covers the endoluminal prosthesis 50 when loaded in the catheter 20. An atraumatic tapered distal tip 29 is coupled to the distal end of the inner member 27, for directing the catheter 20 through the vasculature. The sheath 26 is provided to cover the endoluminal prosthesis 50 (FIGS. 2 and 3) when it is tracked through a body lumen to the deployment site. The sheath 26 is retractable from a position over the inner member 27 so that the prosthesis 50 (FIGS. 2 an 3) can be released at the deployment site. As illustrated in FIG. 1A, the sheath 26 is in a retracted position.

Figure 1B:
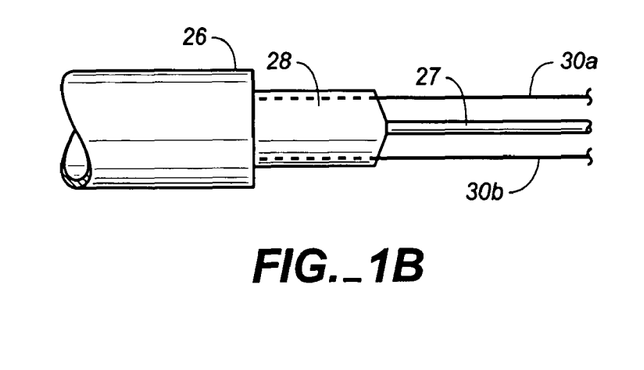
FIG. 1B is an enlarged cross sectional view of a portion of the delivery catheter of FIG. 1A.

Referring to FIG. 1B, elongate stiffening elements 30a, 30b are coupled to the inner member 27 by a bonded region 28 at the distal portion 25 of the catheter 20. The elongate stiffening elements 30a, 30b extend from the bonded region 28, distally towards the proximal end 29a of the tapered distal tip 29.

Referring to FIGS. 2 and 3A, the prosthesis 50 comprises: a tubular graft 55; radially compressible annular support members 52 attached to and supporting the end 51 of tubular graft 55; and an unsupported portion 56 or length of the tubular graft. Although the length of the unsupported portion 56 may vary, in this particular embodiment, the unsupported length (or lengths) is approximately 1 to 2 cm. The annular support members 52 support graft 55 at the end 51 of the prosthesis and/or bias the end 51 of the prosthesis 50 into conforming fixed engagement with an interior wall of a body lumen (not shown) while the unsupported portion 56 is flexible permitting placement of the prosthesis in a highly curved anatomy and reducing stresses on the prosthesis 50. The annular support members 52 are preferably spring members having a predetermined radii and are preferably constructed of a material such as nitinol in a superelastic, shape set, annealed condition attached to the graft by a series of sutures. The graft material is thin-walled so that the prosthesis may be compressed into a small diameter, yet is capable of acting as a strong, leak-resistant fluid conduit when expanded to a cylindrical tubular form The prosthesis 50 further comprises pockets 57a, 57b formed of graft material sewn onto the inner circumference of the tubular graft 55 adjacent the annular support members 52 at the end 51 of the prosthesis 50. The pockets 57a, 57b receive the ends of the stiffening elements 30a, 30b of the catheter 20 which engage the ends 58a, 58b of the pockets 57a, 57b when the sheath 26 is retracted from the prosthesis 20, thus holding the stiffening elements 30a, 30b in place during deployment. The pockets 57a, 57b may be formed in a variety of different shapes where they are configured to receive the stiffening elements 30a, 30b to provide support for the unsupported region during deployment. The pockets 57a, 57b are generally opposite each other on the circumference of the graft 55, and are generally evenly spaced from each other about the circumference of the tubular graft 55. The pockets 57a, 57b, while shown sewn onto the inner circumference of the graft material, may also be sewn on to the outer circumference of the graft material. Other receiving elements or coupling mechanisms may be used, for example, pleats of tubular graft may be attached to the prosthesis. The receiving elements or coupling mechanism may be attached to tubular graft or be attached one or more of the support members. The receiving elements or coupling mechanism may also be located on the outside of the prosthesis.

The stiffening elements 30a, 30b may be constructed of a material such as stainless steel, nitinol, or stiff plastic. The stiffening elements 30a, 30b are generally opposite each other and are spaced from each other in the same configuration as the pockets 57a, 57b are on the prosthesis 50.

Figure 3B:
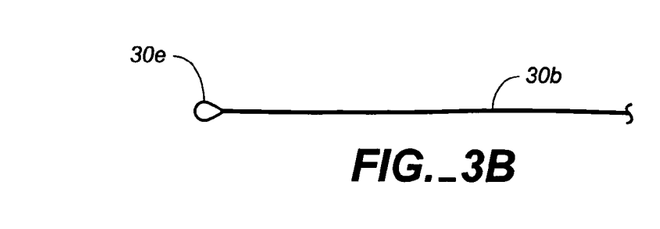
FIG. 3B is a side schematic view of the end of a stiffening element illustrated in FIG. 3A.

FIG. 3B illustrates the stiffening element 30b shown in FIG. 3A in use with a catheter 20. The stiffening element 30b has an atraumatic, rounded end 30e which may be constructed, for example, from a ball of polymer, a bead of solder or wire, or the like. The atraumatic tip reduces possible damage to the stent graft material and/or the body lumen as the catheter 20 is being used.

Various shapes of stiffening elements may be used, preferably so that the stiffening elements provide a low profile within the catheter and so that the stiffening elements do not cause significant trauma to the vessel or endoluminal prosthesis. The stiffening elements in one embodiment according to the invention are between 0.012 inches and 0.035 inches in diameter. The stiffening elements may be bonded to the inner member for example, with a heat shrink, by crimping on the inner member with a metal hypotube, or by gluing on the inner member. At least one stiffening element is used. A plurality of stiffening elements may be used. The stiffening elements can be staggered in some relationship to each other to provide a relatively even distribution of forces when deploying the prosthesis.

The annular support member or members, for example, may be formed of an undulating or sinusoidal patterned wire ring, a series of connected compressible diamond structures or other compressible spring member biased in a radially outward direction, which when released, biases the prosthesis into conforming fixed engagement with an interior surface of the vessel. Annular support members are used to create a seal between the prosthesis and the inner wall of a body lumen as well as to support the tubular graft structure. The annular springs are preferably constructed of nitinol. Examples of such annular support structures are described, for example, in U.S. Pat. Nos. 5,713,917 and 5,824,041 incorporated herein by reference. When used in an aneurysm exclusion device, the support structures have sufficient radial spring force and flexibility to conformingly engage the prosthesis with the body lumen inner wall, to avoid excessive leakage, and prevent pressurization of the aneurysm, i.e., to provide a leak-resistant seal. Although some leakage of blood or other body fluid may occur into the aneurysm isolated by the prosthesis, an optimal seal will reduce the chances of aneurysm pressurization and resulting rupture.

The annular support members are attached or mechanically coupled to the graft material along the tubular graft by various means, such as, for example, by stitching onto either the inside or outside of the tubular graft.

In use, the prosthesis 50 is preloaded into the catheter 20 with the annular support members 52 being held in a radially compressed configuration. A thin flexible sheath 26 is placed over the prosthesis 50 to restrain the prosthesis and prevent it from damaging or catching on the luminal wall as it is delivered to the aneurysm site. The prosthesis 50 is delivered in a compressed state via catheter 20 through a surgically accessed vasculature, to the desired deployment site. When the distal portion 25 of the catheter 20 is located at the deployment site the prosthesis 50 is deployed.

In FIG. 3A, a prosthesis 50 is shown as it is being deployed from the catheter 20. The sheath 26 is retracted from its position over the prosthesis 50 and the end 51 of the prosthesis expands to engage the inner wall of the body lumen (not shown). The stiffening elements 30a, 30b (at least the end portions) are positioned in the pockets 57a, 57b engaging the ends 58a, 58b of the pockets 57a, 57b, respectively. The stiffening elements 30a, 30b are long enough in this embodiment to span the unsupported region 56 of the prosthesis 50 to support it prior to and during deployment and after being released from the sheath 26. Thus, the stiffening elements 30a, 30b prevent longitudinal compression, kinking or folding of the unsupported region 56 of the prosthesis 50 during deployment by providing a force to fix the proximal end 51 of the prosthesis to oppose the retraction force associated with the retraction of the sheath 26.

Figure 4A:
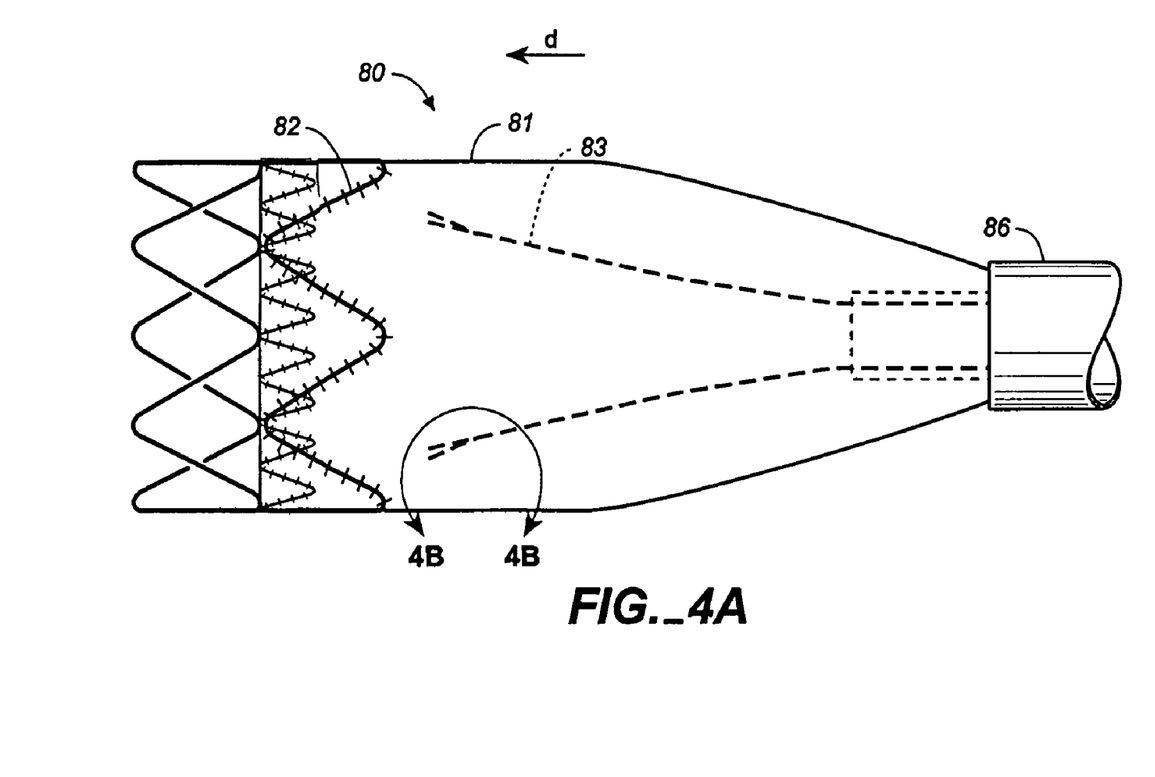
FIGS. 4A-4B illustrate an embodiment of an endoluminal prosthesis with a coupling mechanism for removably coupling a stiffening element to the endoluminal prosthesis.
Figure 4B:
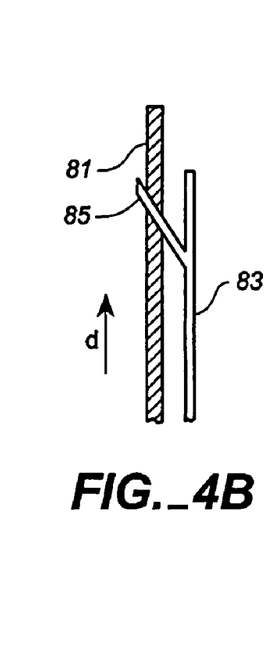

FIGS. 4A-4B illustrate a variation of a prosthesis and coupling device according to the invention. The prosthesis 80 comprises a tubular graft material 81 with at least one distal support member 82 attached thereto. A plurality of stiffening elements 83 are coupled to a catheter 86 in a similar manner as the stiffening elements 30a 30b are attached to the catheter 20 as described herein with reference to FIGS. 1A-3B. As shown here, stiffening elements 83 may shorter than those shown in FIG. 3A such that before deployment the distal end of the inner member is positioned inside the prosthesis 80. The stiffening elements 83 each have a barb 85 on its distal end that is configured to engage the tubular graft material 81. The barb 85 has a sharp tip and is oriented (i.e., facing the graft material 81 and distally extending at an oblique angle) with respect to the stiffening element 83 so that when a pushing force is applied to a stiffening element 83 to push the prosthesis in a direction d out of the catheter 86 (i.e., distally) as shown in FIG. 4A, the barb 85 engagably couples to the tubular graft 81. The stiffening element 83 may then be pulled in a direction towards the catheter (i.e., proximally) whereby the stiffening element 83 is released from engagement with the tubular graft material 81 and thus the stiffening elements 83 are removably coupled to the graft material 81.

Figure 5A:
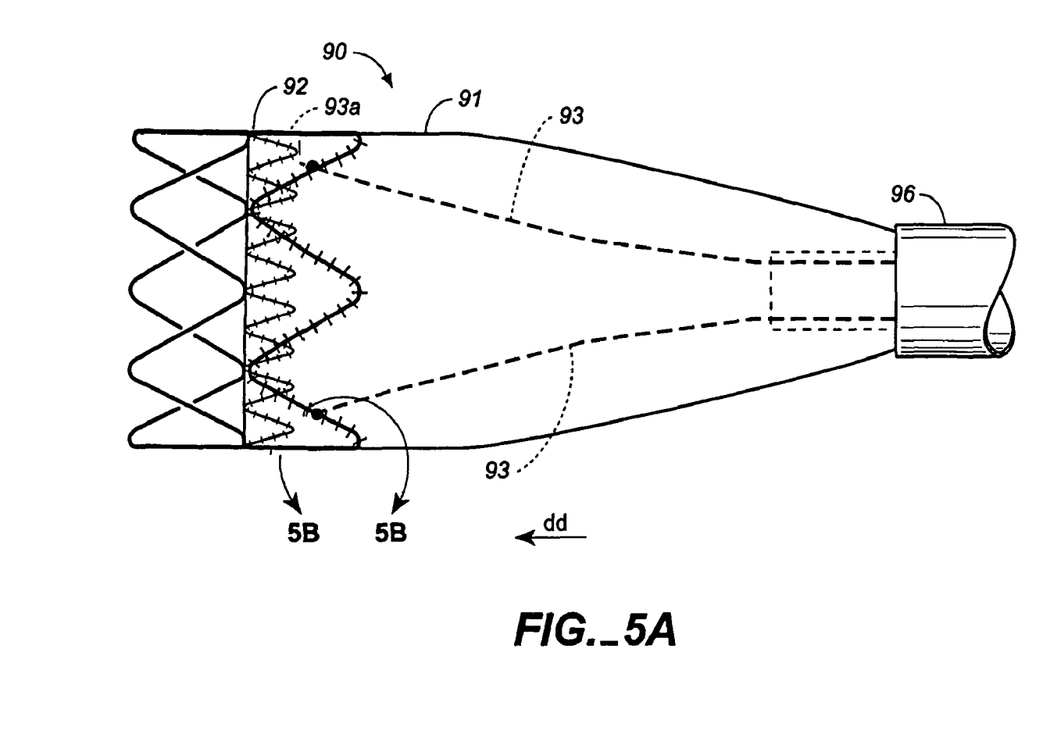
FIGS. 5A-5B illustrate another embodiment of an endoluminal prosthesis with a coupling mechanism for removably coupling a stiffening element to the endoluminal prosthesis.
Figure 5B:
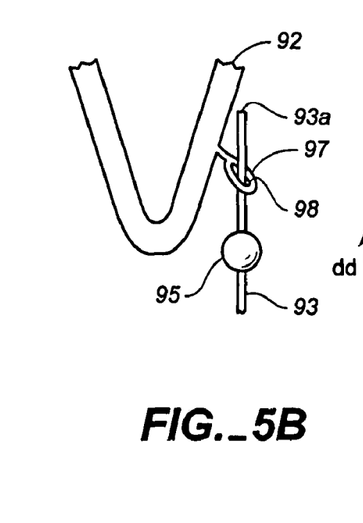

FIGS. 5A-5B illustrate a variation of a prosthesis and coupling device according to the invention. The prosthesis 90 comprises a tubular graft material 91 with at least one distal support member 92 attached thereto. A plurality of stiffening elements 93 are coupled to a catheter 96 in a similar manner as the stiffening elements 30a 30b are attached to the catheter 20 as described herein with reference to FIGS. 1A-3B. The distal support member 92 further comprises a plurality of loops 97 with openings 98 therethrough, attached to the support member 92 by welding or is manufactured by cutting loops 97 out of the support member substrate metal during the manufacturing of the support member 92. The stiffening elements 93 are inserted through the loops 97 so that a distal end 93a of each stiffening element 93 extends distally out of or through a loop 97. Each stiffening element 93 has a ball 95 fixed to it. The ball (or other structure that prevents the stiffening element 93 from extending further through the loop) is located proximally of the opening 98 in the loop 97. The ball 95 is sized larger than the opening 98 in the loop 97 so that when a force is applied to a stiffening element 93 and to the prosthesis 90 in a direction dd (i.e., distally), to resist the retraction force of the catheter, as shown in FIGS. 5A and 5B, force is transmitted by the ball 95 engagably coupling to the loop 97. Once the sheath retraction is complete, the stiffening element 93 may then be pulled in a direction towards the catheter 96 (i.e., proximally) whereby the stiffening element 93 is released from the loop 97 and thus the stiffening elements 93 are removably coupled to the support member 92 of the prosthesis 90.

Figure 6:
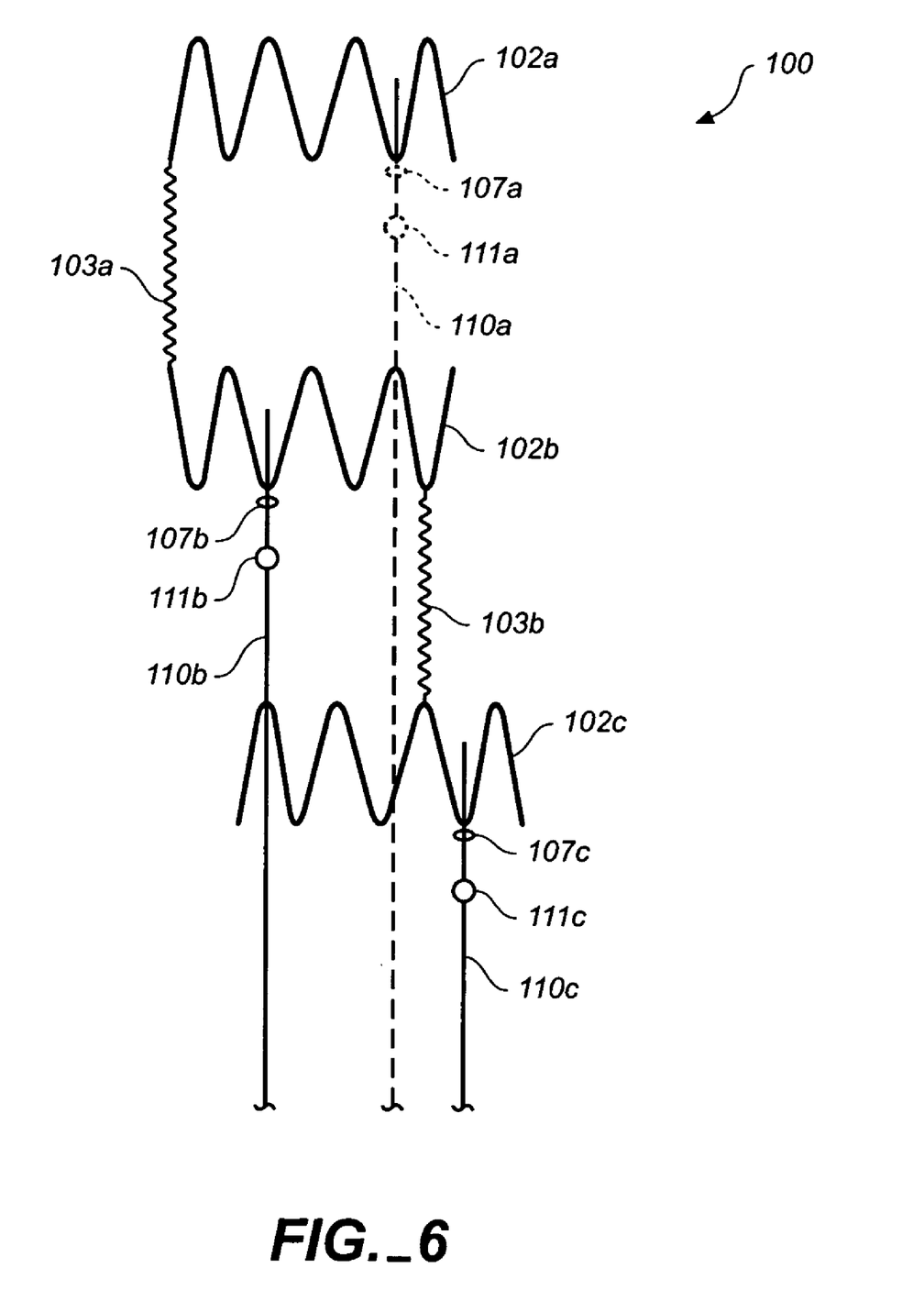
FIG. 6 illustrates an endoluminal prosthesis with a coupling mechanism for removably coupling a stiffening element to the endoluminal prosthesis.

FIG. 6 illustrates an endoluminal prosthesis 100 with removable stiffening elements 110a-c coupled to the prosthesis 100. The prosthesis comprises a stent that may be either balloon expandable or self-expanding. The prosthesis 100 is tubular, comprising a plurality of annular members 102a-c and flexible connectors 103a-b connecting adjacent annular members 102a, 102b and annular members 102b, 102c, respectively at locations generally evenly spaced from adjacent flexible connectors about the circumference of the prosthesis 100. The flexible connectors 103a-b while connecting the annular members 102a,b,c bend and flex when deployed, to permit the prosthesis 100 to conform to tortuous body lumens.

A plurality of stiffening elements 110a-c are coupled to a catheter (not shown) in a similar manner as the stiffening elements 30a, 30b are attached to the catheter 20 as described herein with reference to FIGS. 1A-3B. The stiffening elements 110a-c are generally evenly spaced from adjacent stiffening elements about the circumference of the prosthesis. The stiffening elements 110a-c have balls 111a-c respectively, fixed thereto, similar to the ball 95 described above and are removably coupled to annular members 102a-c, respectively through loops 107a-c, respectively having openings 108a-c, respectively, and in a manner similar to stiffening elements 93 and loops 97 described herein with reference to FIGS. 5A-5B.

The prosthesis 100 may be a self-expanding stent that is deployed by releasing the stent from a restraining mechanism. The stiffening elements 110a-c support the flexible regions of the stent defined by flexible connectors 103a-c when the stent is both loaded and deployed.

Surgical methods and apparatus for accessing the surgical site are generally known in the art and may be used to place the catheter within the vasculature and deliver the prosthesis to the deployment site. Additionally, various actuation mechanisms for retracting sheaths and inflating balloons of balloon catheters are known in the art. The prosthesis may be delivered to the deployment site by one of several ways. The catheter is inserted into the artery and guided to the deployment site using fluoroscopic imaging where the device is then deployed. The annular support members supporting the graft, biased in a radially outward direction, are released to expand and engage the prosthesis in the vessel against the vessel wall to prop open the vessel in the case of a stent or to provide an artificial lumen for the flow of blood in the case of a stent graft.

While the invention has been described with reference to particular embodiments, it will be understood to one skilled in the art that variations and modifications may be made in form and detail without departing from the spirit and scope of the invention. Particular attachment, coupling and restraining mechanisms have been described. However, numerous other coupling mechanisms may be used to removably couple the stiffening elements to the prosthesis.

The invention claimed is:

1. An endoluminal prosthesis delivery system comprising:
a stent-graft including a support member, graft material attached to the support member, and a pocket coupled to the graft material, wherein the pocket is formed the graft material, and wherein the stent-graft comprises an unsupported portion of the graft material without a support member attached to the graft material anywhere along the circumference of the stent-graft at the unsupported portion; and
a delivery catheter comprising:
a distal portion configured to hold and deploy the stent-graft, and to track through a body lumen,
a sheath covering the stent-graft, and
at least one stiffening element having a first end coupled to the distal portion and a free end extending along a length of the distal portion, wherein the free end is configured to be removably coupled to the pocket such that the stiffening element resists a proximally directed force on the stent-graft as the sheath is removed from the stent-graft, wherein the free end is removably coupled to the stent-graft such that proximal movement of the distal portion disengages the stiffening element from the stent-graft, and wherein the at least one stiffening element extends along the unsupported portion of the graft material to support the unsupported portion when the free end is disposed in the pocket.

* * * * *